(12) United States Patent
Homan et al.

(10) Patent No.: US 8,771,274 B2
(45) Date of Patent: Jul. 8, 2014

(54) SURGICAL DRILL FOR PROVIDING HOLES AT AN ANGLE

(75) Inventors: Bradley Michael Homan, Celebration, FL (US); Rickey Hart, Marco Island, FL (US)

(73) Assignee: Karl Storz GmbH & Co. KG (DE)

( * ) Notice: Subject to any disclaimer, the term of this patent is extended or adjusted under 35 U.S.C. 154(b) by 40 days.

(21) Appl. No.: 13/297,590

(22) Filed: Nov. 16, 2011

(65) Prior Publication Data

US 2012/0059379 A1 Mar. 8, 2012

Related U.S. Application Data

(62) Division of application No. 12/337,284, filed on Dec. 17, 2008.

(60) Provisional application No. 61/014,188, filed on Dec. 17, 2007.

(51) Int. Cl.
*A61B 17/00* (2006.01)
*A61B 17/16* (2006.01)
*A61B 17/17* (2006.01)

(52) U.S. Cl.
USPC ............ 606/80; 606/86 R; 606/87; 606/88

(58) Field of Classification Search
USPC .............. 606/53–105.5; 623/13.11–13.14
See application file for complete search history.

(56) References Cited

U.S. PATENT DOCUMENTS

| | | | |
|---|---|---|---|
| 5,002,546 A | 3/1991 | Romano | |
| 5,320,115 A | 6/1994 | Kenna | |
| 5,320,626 A | 6/1994 | Schmieding | |
| 5,395,188 A | 3/1995 | Bailey et al. | |
| 5,464,407 A * | 11/1995 | McGuire | 606/86 R |
| 5,514,157 A | 5/1996 | Nicholas et al. | |
| 5,643,273 A | 7/1997 | Clark | |
| 5,688,276 A * | 11/1997 | Shaffer | 606/916 |
| 5,755,718 A * | 5/1998 | Sklar | 606/80 |
| 5,968,050 A | 10/1999 | Torrie | |
| 7,815,646 B2 | 10/2010 | Hart | |
| 8,282,647 B2 * | 10/2012 | Re | 606/89 |
| 2008/0249481 A1 * | 10/2008 | Crainich et al. | 604/264 |
| 2009/0287219 A1 * | 11/2009 | Hart | 606/96 |
| 2012/0265205 A1 * | 10/2012 | Steiner et al. | 606/80 |

FOREIGN PATENT DOCUMENTS

| | | |
|---|---|---|
| EP | 2005905 A1 | 12/2008 |
| FR | 2692467 A1 | 12/1993 |

OTHER PUBLICATIONS

Smith & Nephew, Inc., Clancy Anatomic Cruciate Guide, 2007 (2 pages).
European Search Report; Application No. EP 08 02 1888; Apr. 15, 2011; 6 pages.

* cited by examiner

*Primary Examiner* — Kevin Truong
*Assistant Examiner* — Nicholas Woodall
(74) *Attorney, Agent, or Firm* — St. Onge Steward Johnston & Reens LLC

(57) ABSTRACT

A surgical drill for providing holes at an angle for use in repair and replacement of the ACL is disclosed, generally comprising a drill guide having a head that is angularly adjustable with respect to a body, a flexible guide pin and a flexible drill. The adjustable head of the drill guide allows a surgeon to drill a hole in the femur at an angle to a tunnel provided in the tibia. Because the surgeon can access the femur via the hole in the tibia, the surgical drill of the present invention obviates the need for a second hole in the tissue and also makes placement of femur hole more precise for securement of the ligament or tendon graft within the hole.

11 Claims, 8 Drawing Sheets

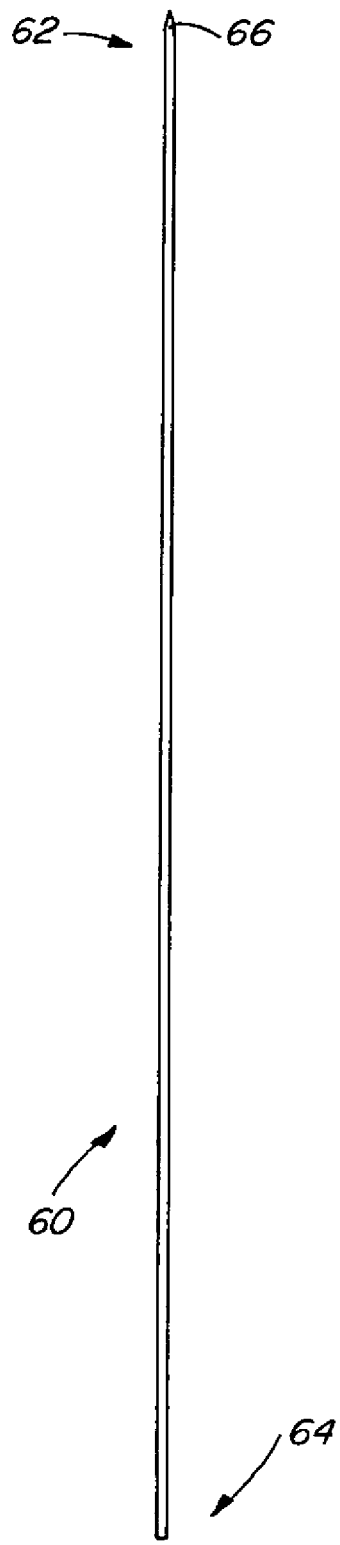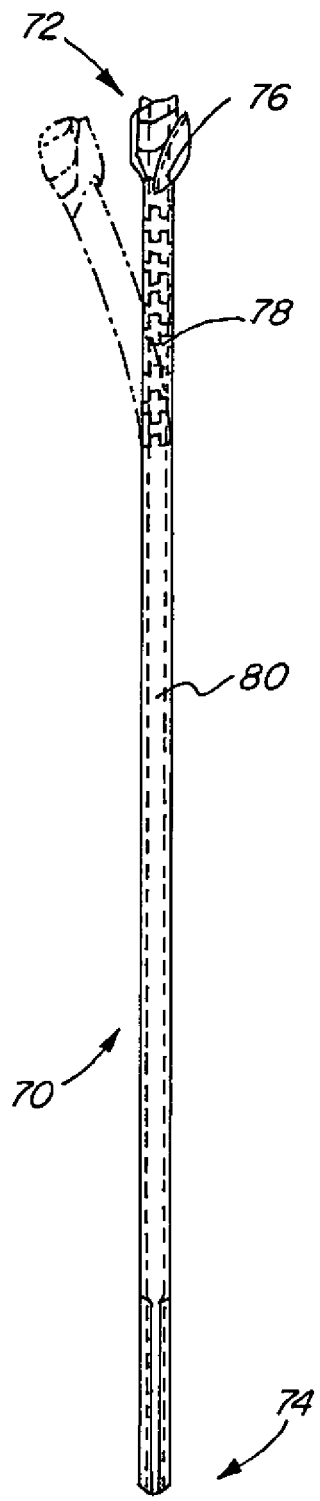
FIG. 2                    FIG. 3

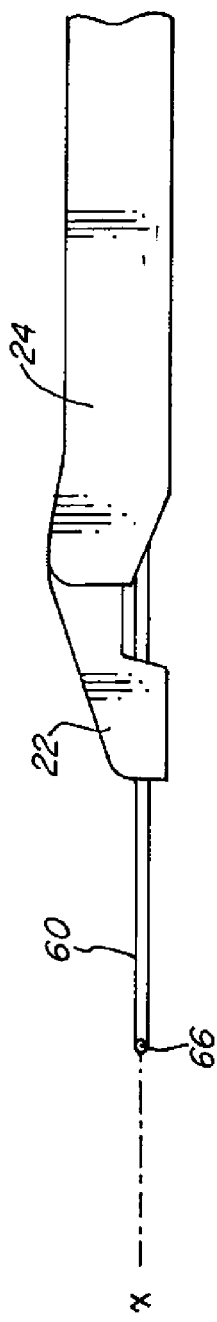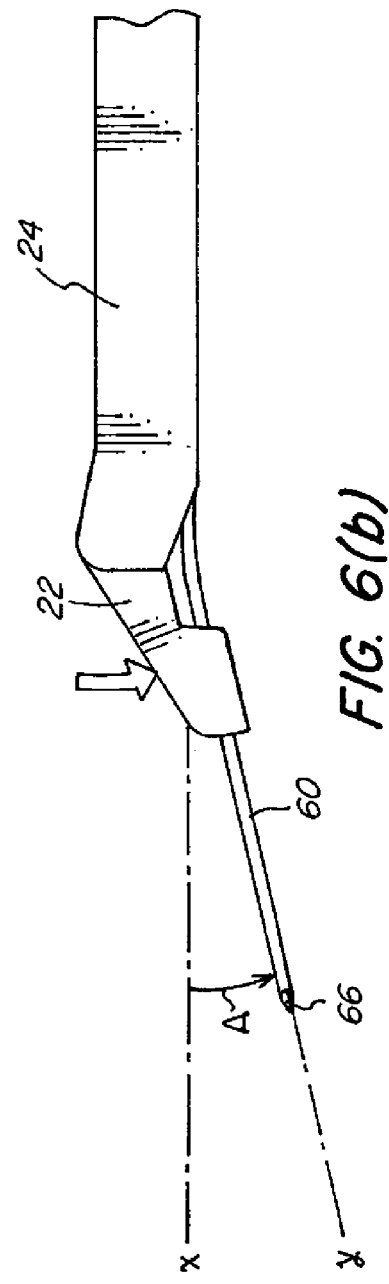
FIG. 6(a)
FIG. 6(b)

SURGICAL DRILL FOR PROVIDING HOLES AT AN ANGLE

CROSS-REFERENCE TO RELATED APPLICATIONS

The present application is a divisional of pending U.S. patent application Ser. No. 12/337,284, filed on Dec. 17, 2008, which claims the benefit under 35 U.S.C. §119(e) of the U.S. Provisional Patent Application No. 61/014,188 filed on Dec. 17, 2007. The content of all prior applications is incorporated herein by reference.

FIELD OF THE INVENTION

The present invention relates to a surgical drill. More specifically, the invention relates to a surgical drill for providing a second hole in a bone at an angle relative to a first hole drilled in a bone.

BACKGROUND OF THE INVENTION

Damage to ligaments, such as anterior cruciate ligaments (ACL) and the posterior cruciate ligaments (PCL), cartilage, and tendons has become a relatively common occurrence and often requires surgical repair. Often, the ACL or the PCL is ruptured or torn as a result of physical activity and, consequently, various surgical procedures have been developed for replacing or reconstructing these ligaments.

The knee joint is often repaired by substituting a harvested or synthetic replacement ligament for the damaged one. Commonly, a substitute ligament or graft is inserted into tunnels reamed in the femur and tibia bones. Once anchored in place, the graft ligament is able to cooperate with the surrounding bone and tissues and thereby perform the functions of the damaged ACL or PCL. One problem associated with this technique is locating the proper position and angle for drilling the tunnel in the femur (femoral tunnel). Several methods have been developed for determining the location for drilling the femoral tunnel.

One such method is to insert a drill guide and guide pin through the incision and tunnel in the tibia and into the femur. In order to accurately shoot a guide pin for femoral tunnel preparation, most surgeons use an "over the top" drill guide, as shown in U.S. Pat. No. 5,320,115 to Kenna and U.S. Pat. No. 5,320,626 to Schmieding. This type of drill guide references the back wall of the femoral notch to deliver the guide pin a certain distance in millimeters from the back wall. The distance desired is chosen by the surgeon depending on the diameter of the ACL graft to be used. A reamer will be used over the guide pin to create the femoral tunnel, and 2 mm of back wall or less should be present behind the tunnel. It is undesirable to ream through the back wall and in many cases the chosen fixation method will not work if this occurs. For example, if an 8 mm ACL graft is to be used then a 6 mm over the top guide is selected. This will place the guide pin 6 mm from the back wall. When an 8 mm reamer is used over the guide pin, then 2 mm of back wall will remain.

Traditionally the over the top guide is placed through the drilled tibial tunnel to position the guide easily on the back wall. When the tibial tunnel is drilled properly, however, the over the top guide is fairly vertical in the notch in the frontal plane because the placement of the guide is dictated by the angle of the tibial tunnel. Recent studies are indicating that a more lateral femoral tunnel placement is desirable. Yet, this angle is difficult to reach when using a traditional over the top guide in the tibial tunnel, so some surgeons are recommending using a second low medial portal to place the over the top guide. This allows for more lateral positioning in the AP plane, but, consequently, starting more superior decreases the angle of pin placement in the lateral plane, increasing the chance of reaming through the back wall of the femur.

While the medial portal can be used, and has the advantage of allowing for a more lateral femoral tunnel, it has several disadvantages that make it undesirable. Notably, using the medial portal involves making a second incision in the tissue, which results in unnecessary fluid loss and an additional scar. Furthermore, in order to use the medial portal, hyperflexion of the knee must be performed which is sometimes difficult to do. Also, while some have probably begun designing new instruments and techniques for those who are comfortable using the medial portal, most surgeons are most familiar and most comfortable with using the tibial tunnel as a reference for placing the femoral tunnel. These surgeons are not likely to drastically change the technique they are comfortable with. Last, as stated above, using the medial portal increases the chance of reaming through the back wall of the femur which can make it difficult or impossible to properly secure the graft ligament. Using the tibial tunnel as a reference puts the guide pin in a safe trajectory so that the back wall will not be violated during reaming.

It is therefore desirable to have a surgical drill which uses the tibial tunnel as a reference for placing the femoral tunnel. In addition, it is desirable to have a drill guide which allows for more lateral femoral tunnel placement.

SUMMARY OF THE INVENTION

Accordingly, it is an object of the present invention to provide a method for drilling a tunnel in a human femur at an angle relative to a tunnel drilled in the tibia.

It is a further object of the present invention to provide a surgical drill which allows a user to drill a tunnel in a femur at an angle to a tunnel in the tibia.

It is yet a further object of the present invention to provide a drill guide having a head that is angularly adjustable relative to the body, thus allowing a user to drill a tunnel in a femur at an angle to a tunnel in the tibia.

These and other objects and advantages are achieved by providing a surgical drill comprising a drill guide, a guide pin, which may be made of a flexible material, and a drill, which may also be flexible. The drill guide comprises a body and a head rotatably mounted to the body at a pivot point which allows a user to drill along an axis x and thereafter also along an axis y. The drill guide may further comprise a longitudinal channel passing through said body and into the head for releasably accepting the guide pin.

In addition, the drill guide may also comprise an actuator, comprising a rod, a screw having external threads, and a knob threadably connected to the screw, for adjusting the angular orientation of the head with respect to the body. At a distal end, the rod may be connected to the head of the drill guide and may be connected at a proximal end to the screw. The rod may pass through the body of the drill guide. Rotation of the knob may cause the screw and the rod to advance in a distal direction or retract in a proximal direction, further causing the head to rotate about a pivot point. To allow for rotation of the head, the rod may be connected to the head at a point radially spaced from the pivot point. In one embodiment, clockwise rotation of said knob causes the screw and the rod to advance in a distal direction, further causing the head to rotate clockwise about a pivot point. In another embodiment, counterclockwise rotation of the knob causes the screw and the rod to retract in a proximal direction, further causing the head to rotate counter-clockwise about a pivot point.

A drill guide comprising a body, a head rotatably mounted to said body at a pivot point for permitting drilling along an axis x and thereafter also along an axis y, and an actuator for adjusting the angular orientation of the head with respect to the body is also provided. In one embodiment, the drill guide further comprises a longitudinal channel passing through said body and into said head for releasably accepting a guide pin. In another embodiment, the drill guide further comprises a handle located adjacent to the body. In yet another embodiment, the actuator comprises a rod, a screw, and a knob threadably connected to the screw, for adjusting the angular orientation of the head with respect to the body.

A method of drilling a hole in a human femur is also provided, comprising the steps of: providing a hole in a human tibia along an axis x; providing a surgical drill comprising a guide pin, a drill guide for accepting said guide pin, and a drill, wherein the drill guide allows a user to drill a hole in a human femur at an angle relative to the hole in the tibia; inserting the drill guide into the hole in the tibia; inserting the guide pin into the drill guide until the pin comes into contact with and is anchored to the femur; removing the drill guide from the hole in the tibia while leaving the guide pin anchored to the femur; inserting the drill around the anchored guide pin until the drill comes into contact with the femur; drilling a hole in said femur along an axis y, at an angle relative to axis x.

In one embodiment, the drill guide comprises a body and a head rotatably mounted to the body. The method may also comprise the step of adjusting the angle of the drill guide head with respect to the body until a desired angle is achieved.

BRIEF DESCRIPTION OF THE DRAWINGS

FIG. 2 is a side view of an embodiment of the guide pin as used with the surgical drill of the present invention.

FIG. 3 is a side view of an embodiment of the flexible drill as used with the surgical drill of the present invention.

FIG. 6(a) is a side view of an embodiment of the drill guide as used with the surgical drill of the present invention, showing the head aligned along an axis x.

FIG. 6(b) is a side view of an embodiment of the drill guide as used with the surgical drill of the present invention, showing the head aligned along an axis y, at an angle A to axis x.

DETAILED DESCRIPTION OF THE INVENTION

Figure 1:
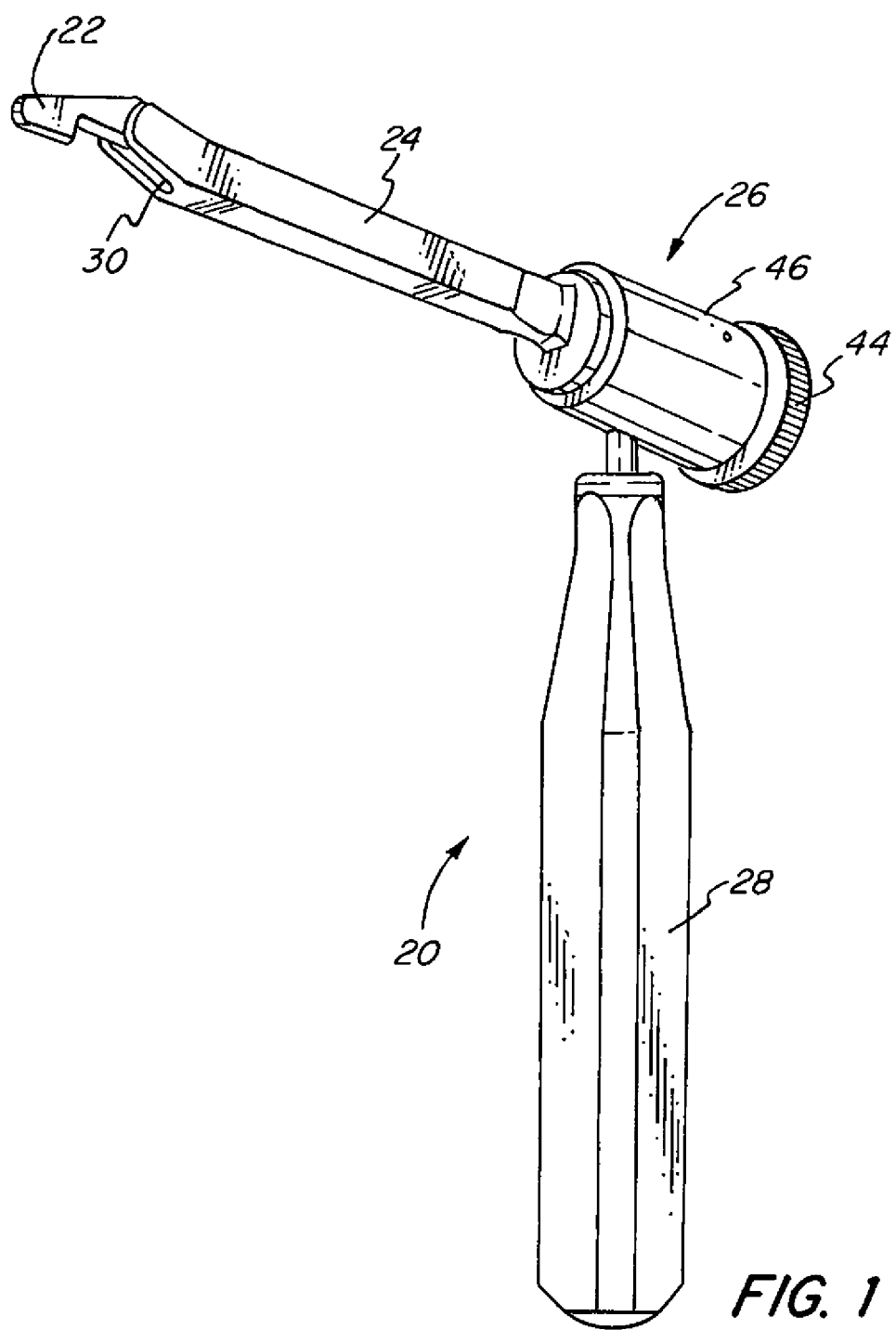
FIG. 1 is a perspective view of an embodiment of the drill guide as used with the surgical drill of the present invention.
Figure 4:
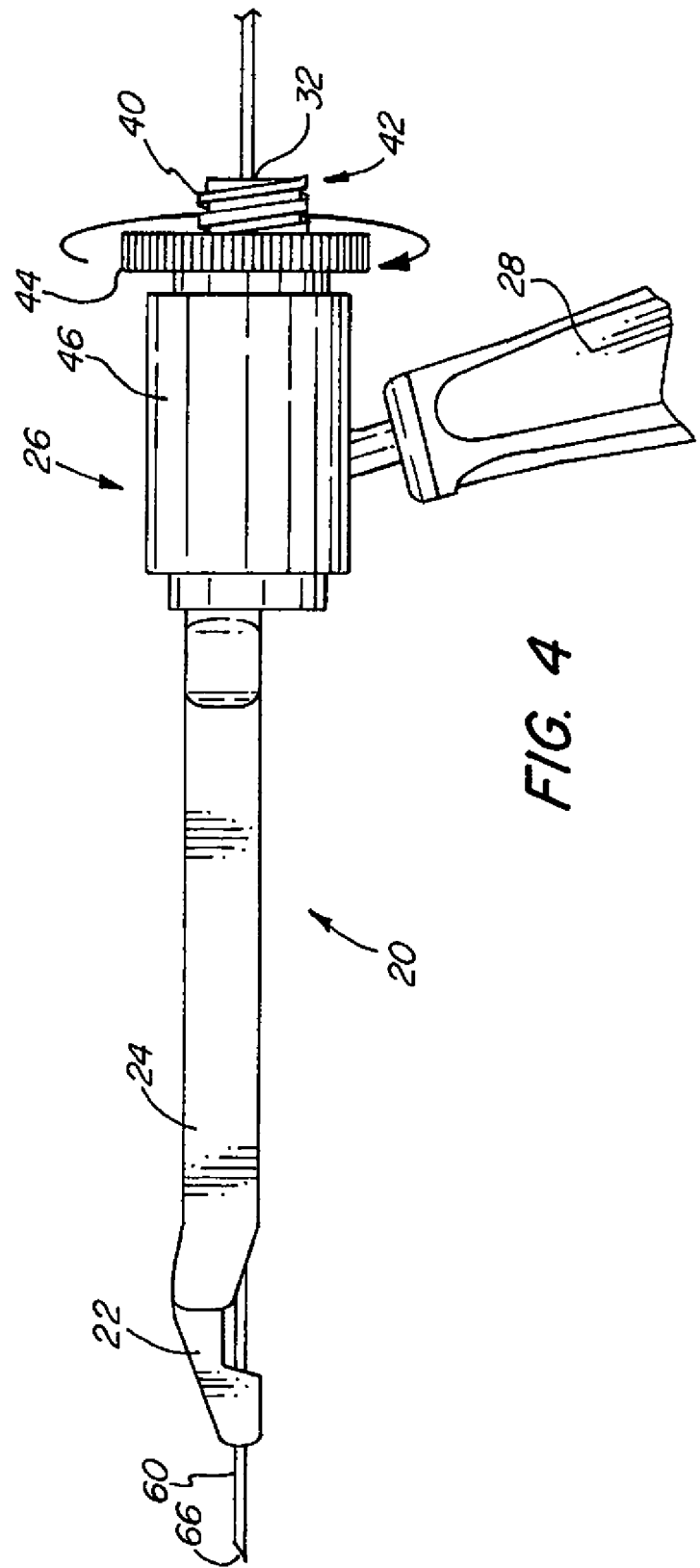
FIG. 4 is a side view of an embodiment of the drill guide as used with the surgical drill of the present invention.

FIGS. 1-3 depict the surgical drill in accordance with the present invention, which comprises drill guide 20, pin 60, and flexible drill 70. The surgical drill of the present invention provides a second hole along an axis y that may be at an angle relative to a first hole along an axis x. More specifically, particularly in view of the problems associated with the prior art described herein, the surgeon can drill a tunnel in the femur at an angle relative to a tunnel in the tibia. Because the surgeon can access the femur via the tunnel in the tibia, the surgical drill of the present invention obviates the need for a second hole in the tissue and also makes placement of femoral tunnel 90 more precise for securement of the ligament or tendon graft within the tunnel. As discussed in the prior art, placement of the femoral tunnel was problematic and poor placement may lead to improperly secured ligaments or tendons.

Figure 5:
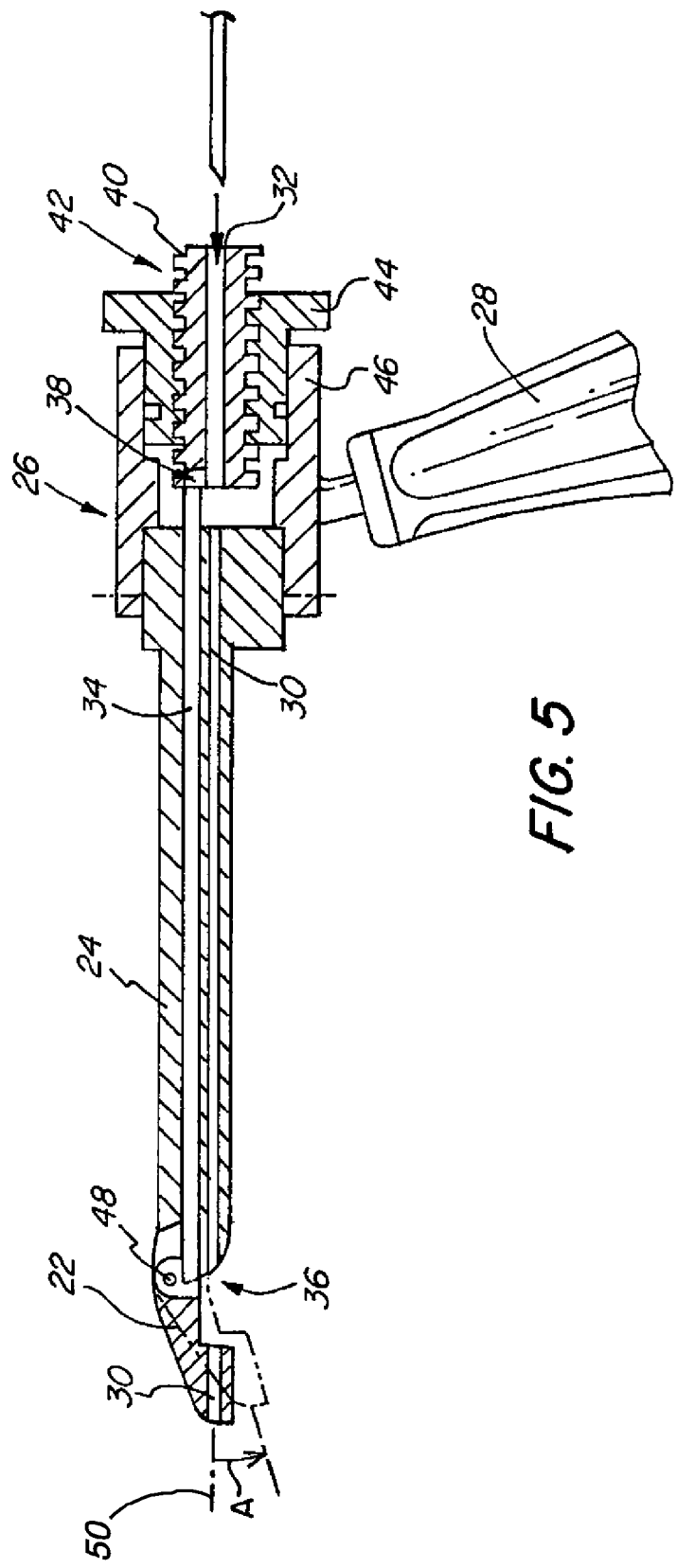
FIG. 5 is a side sectional view of an embodiment of the drill guide as used with the surgical drill of the present invention.

Referencing FIG. 1, drill guide 20 of the surgical drill comprises a head 22, rotatably connected to a body 24, an actuator assembly 26, a handle 28, and an internal longitudinal channel 30 having an opening 32 for releasably accepting guide pin 60. The channel 30 extends through the body 24 and into the head 22. As shown in more detail in FIG. 5, actuator assembly 26 comprises a rod 34 having a distal end 36 and a proximal end 38, a screw 40 having external threads 42, and a knob 44 threadably connected to the screw 40. The distal end 36 of the rod 34 is connected to the head and the proximal end 38 is connected to the screw 40. The actuator assembly is contained within a housing 46.

To adjust the angle A of head 22 relative to body 24, a user rotates knob 44. Due to their threaded connection, this rotation of the knob 44 translates into linear movement of screw 40 and rod 34. To provide rotation of the head 22 with actuation of the rod 34, the rod is connected to the head at a point radially spaced apart from the pivot point 48 where the head 22 connects to the body 24. In the present embodiment, clockwise rotation of the knob 44 causes the rod 34 to advance towards the distal end 36, which causes the head 22 to accordingly rotate clockwise. Counter-clockwise rotation of the knob 44 causes the rod 34 to retract towards the proximal end 38, which, in turn, causes the head to rotate counter-clockwise. In a preferred embodiment, the ratio of rotation of the knob to angular rotation of the head is 18:1, meaning that for every 18 degrees of rotation of knob 44, angle A will change by 1 degree. Thus, to adjust angle A by 15 degrees, the knob 44 must be rotated by 270 degrees. This ratio provides the user with acceptable precision for adjustment of angle A, yet allows full range of motion of the head with only one turning motion. Other ratios are contemplated herein and could be easily adjusted by one having skill in the art. In addition, other mechanisms, such as a trigger, are contemplated for adjusting the angular orientation of the head 22 with respect to the body 24.

Guide pin 60 of the surgical drill, depicted in FIG. 2, has a distal end 62 and a proximal end 64. Pin head 66, located at the distal end 62, is pointed in the present embodiment so that it may penetrate a patient's femur bone. In an alternative embodiment, distal end 62 may be formed as a screw so that it may be screwed into a patient's femur bone. As shown in FIGS. 6(a) and 6(b), angular adjustment of head 22 causes an angular displacement A of pin 60 with respect to the body 24. Thus, guide pin 60 is made of a flexible material such that it can bend when the angle A of the head 22 of the drill guide 20 is adjusted. However, the material must be rigid enough so that it will maintain its shape when the drill 70 is passed over the guide pin 60.

Drill 70 of the surgical drill, depicted in FIG. 3, has a distal end 72 and a proximal end 74. Located at the distal end 72 is the drill bit 76 and flexible portion 78. An internal channel 80 that runs the length of the drill 70 is also provided so that the drill 70 may be slid over the guide pin 60. Flexible portion 78 allows the drill 70 to pass over the guide pin 60 in a bent shape.

In operation, known methods are used to create a tibial tunnel 86 in the tibia 82 that extends towards the femur 84. Typically, a drill guide specifically designed for drilling tibial tunnels is placed against the tissue. A guide pin is then inserted into the drill guide for piercing the tissue to create a first tissue hole. Once the guide pin is anchored in the tibia, the drill guide is removed and a standard drill is slid over the drill guide and is used to create tibial tunnel 86.

Figure 8:
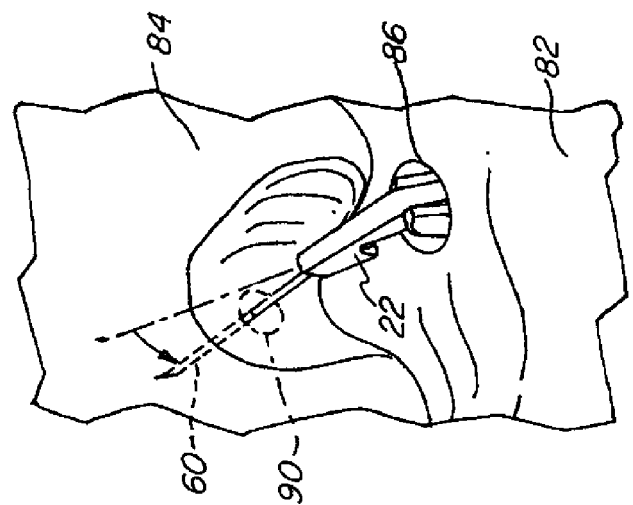
FIG. 8 is a view of an embodiment of the drill guide and guide pin, as used with the surgical drill of the present invention, being used in a human knee.
Figure 7:
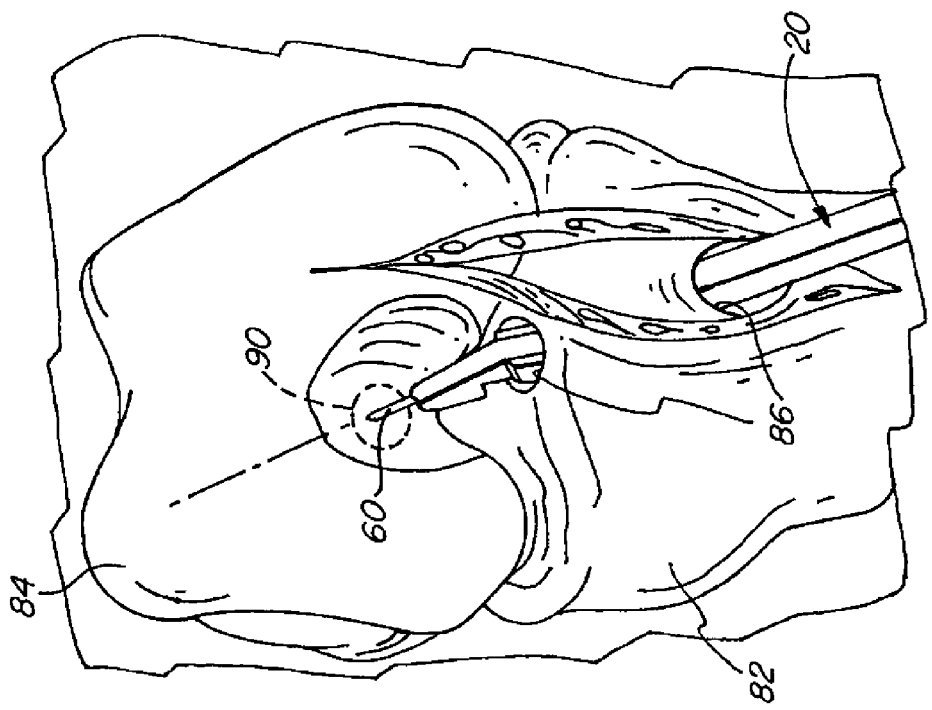
FIG. 7 is a view of an embodiment of the drill guide and guide pin, as used with the surgical drill of the present invention, being used in a human knee.
Figure 10:
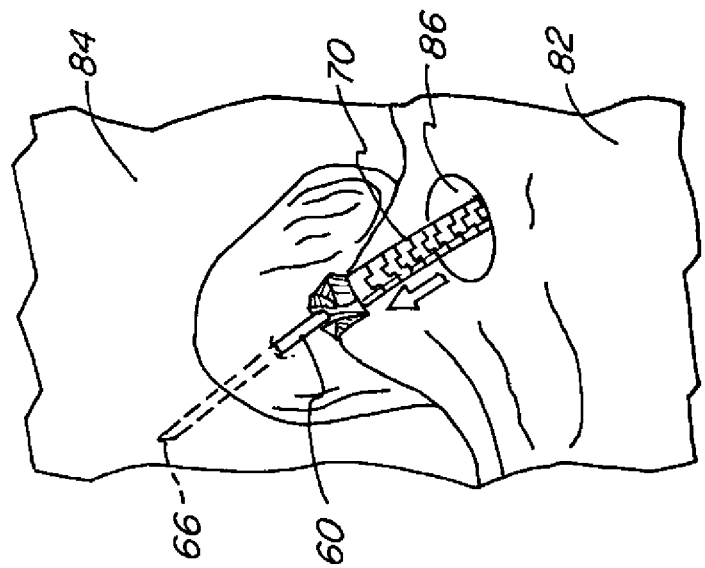
FIG. 10 is a view of an embodiment of the flexible drill and guide pin, as used with the surgical drill of the present invention, being used to drill a tunnel in a human femur bone.

Referring now to FIGS. 7 and 8, to create a femoral tunnel 90, guide pin 60 is inserted into opening 32 of drill guide 20. Together, the drill guide 20 and guide pin 60 are inserted into the tibial tunnel 86 until the guide 20 is in close proximity to the femur and the head 22 has passed through tibial tunnel 86. The user, typically a surgeon, then rotates knob 44 to adjust the angle A of head 22. Because the body 24 of the drill guide 20 remains stationary within the tibial tunnel 86 while the head 22 is free to rotate with respect to the body 24, the drill guide of the present invention allows the user to drill a second (femur) tunnel at an angle to the first (tibia) tunnel. Once a desired angle is achieved, pin 60 is pushed further through the internal channel 30 until pin head 66 passes through the now angled head 22 and in comes in contact with femur 84. Once in contact with femur 84, further force is needed to anchor pin head 66 within femur 84. In some cases, this further force is achieved by drilling the pin through drill guide 20.

Notably, the drill guide of the present invention is versatile in that it provides a surgeon with a large range of angles at which to place the femoral tunnel with respect to the tibial tunnel. Thus, the surgeon is not limited to either drilling a straight femoral tunnel or to drilling the femoral tunnel at a single, fixed angle, as is the case with the straight or fixed angle drill guides of the prior art.

Figure 9:
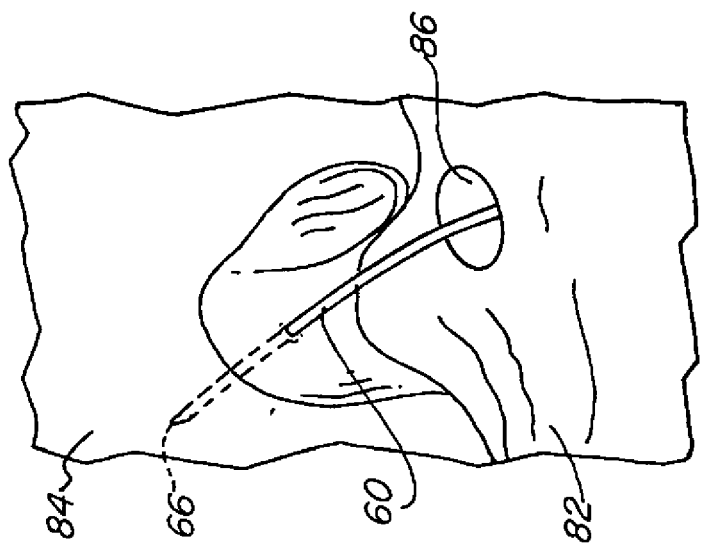
FIG. 9 is a view of an embodiment of the guide pin, as used with the surgical drill of the present invention, anchored in a human femur bone.

Drill guide 20 is then removed by sliding it away from the femur 84 back through the tibial tunnel 86 and away from the patient. As shown in FIG. 9, guide pin 60 is left in place anchored to femur 84. Flexible drill 70 is then inserted around pin 60 toward the patient by passing pin 60 through internal channel 80 of flexible drill 70. The diameter of flexible drill 70 should be the same as or smaller than the diameter of tibia tunnel 86 such that flexible drill 70 passes through tibia tunnel 86 and toward femur 84. It should be understood that pin 60 acts as a guide for leading flexible drill 70 toward femur 84 at the angle set by pin 60 and head 22. Once in contact with femur 84, flexible drill 70 drills femoral tunnel 90 by being rotated about with a standard driller, or machine for rotating a drill bit.

Figure 11:
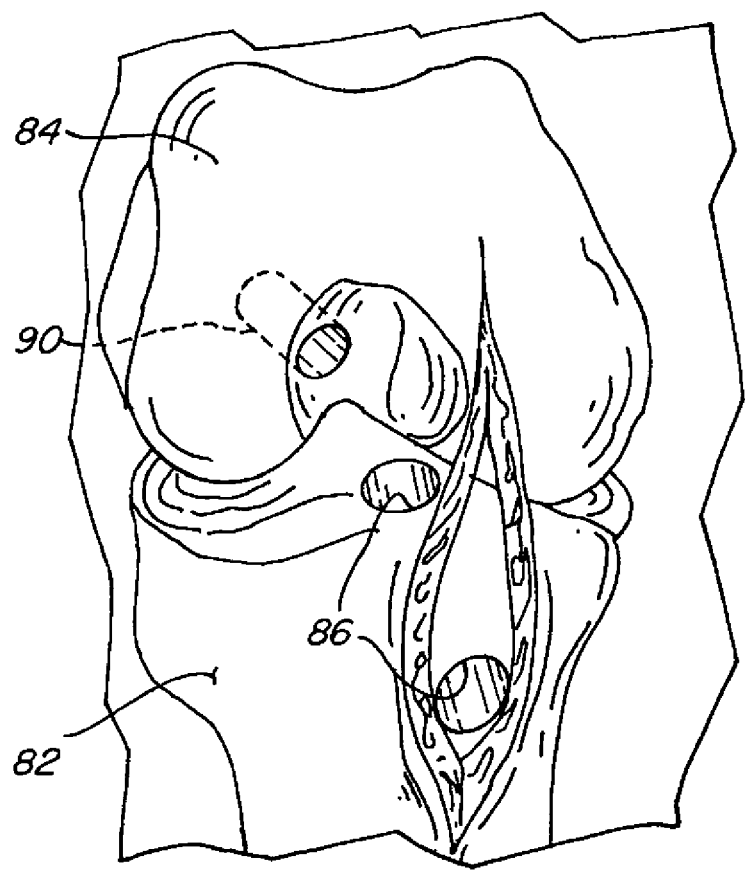
FIG. 11 is a view of a femoral tunnel placed by the surgical drill of the present invention, at an angle relative to a tibial tunnel.

After femoral tunnel 90 is drilled, flexible drill 70 and guide pin 60 are removed from the patient. As shown in FIG. 11, resulting is a femoral tunnel placed at an angle with respect to the tibial tunnel.

In another embodiment, flexible pin 60 and flexible drill 70 are used to drill both tibial tunnel 86 and femoral tunnel 90. This is accomplished by pin 60 first being anchored in tibia 82, at which point the tibia drill guide is removed from pin 60 as described above. Flexible drill 70 is then slid over pin 60, but this time to simply create a straight tunnel, or a tunnel being straight relative to body 24. Since tibial tunnel 86 is straight, either a straight drill (not shown) standard in the industry or prior art, or flexible drill 70 may be used. Once tibial tunnel 86 is created, flexible drill 70 is removed and the drill guide 20 is inserted in order to locate femur hole 90 at an angle relative to tibia tunnel 86. The above description for placing femur hole 90 is then followed.

It should be understood that the foregoing is illustrative and not limiting, and that obvious modifications may be made by those skilled in the art without departing from the spirit of the invention. Accordingly, reference should be made primarily to the accompanying claims, rather than the foregoing specification, to determine the scope of the invention.

What is claimed is:

1. A method of drilling a hole in a human femur comprising the steps of:
    providing a hole in a human tibia along an axis x;
    providing a surgical drill comprising a guide pin, a drill guide for accepting said guide pin, and a drill, said drill guide comprising a body having a first longitudinal axis and a head pivotally mounted to a distal end of said body at a pivot point said pivot point defining a second axis orthogonal to said first longitudinal axis, said head adapted to pivot about said second axis;
    inserting said drill guide into said hole in the tibia;
    inserting said guide pin into said drill guide until the pin comes into contact with and is anchored to the femur;
    removing said drill guide from the hole in the tibia while leaving the guide pin anchored to the femur;
    inserting the drill around the anchored guide pin until the drill comes into contact with the femur;
    drilling a hole in said femur along an axis y, at an angle relative to axis x.

2. The method of claim 1 wherein said drill guide further comprises a longitudinal channel passing through said body and into said head for releasably accepting the guide pin.

3. The method of claim 1 further comprising the step of adjusting the angle of said drill guide head with respect to said body until a desired angle is achieved.

4. The method of claim 1 wherein said drill guide further comprises an actuator for adjusting the angular orientation of the head with respect to the body.

5. The method of claim 4 wherein said actuator comprises:
    a rod;
    a screw; and
    a knob threadably connected to said screw;
    said rod connected at a distal end to the head and connected at a proximal end to the screw, such that rotation of said knob causes said screw and said rod to advance in a distal direction or retract in a proximal direction, further causing said head to rotate about the pivot point.

6. The method of claim 5 wherein said rod further passes through the body of the drill guide.

7. The method of claim 5 wherein said rod is connected to said head at a point radially spaced from the pivot point, such that linear movement of said rod translates into angular rotation of said head.

8. The method of claim 5 wherein clockwise rotation of said knob causes said screw and said rod to advance in a distal direction, further causing said head to rotate clockwise about a pivot point.

9. The method of claim 5 wherein counter-clockwise rotation of said knob causes said screw and said rod to retract in a proximal direction, further causing said head to rotate counter-clockwise about a pivot point.

10. The method of claim 1 wherein said guide pin is made of a flexible material.

11. The method of claim 1 wherein said drill is flexible.

* * * * *